United States Patent [19]

Hayes

[11] 4,431,842

[45] Feb. 14, 1984

[54] CATALYTIC PREPARATION OF NITROALKANES

[75] Inventor: William V. Hayes, Freeport, Tex.

[73] Assignee: The Dow Chemical Company, Midland, Mich.

[21] Appl. No.: 446,076

[22] Filed: Dec. 1, 1982

[51] Int. Cl.³ .............................................. C07C 76/02
[52] U.S. Cl. .................................... 568/948; 568/947
[58] Field of Search ................................ 568/947, 948

[56] References Cited

U.S. PATENT DOCUMENTS 3,115,527 12/1963 Drimus et al. ...................... 568/947

FOREIGN PATENT DOCUMENTS 578044 6/1946 United Kingdom ................ 568/947

OTHER PUBLICATIONS

Hass et al., J. Am. Chem. Soc., vol. 76, pp. 2962 to 2694, (1954).
Coldiron et al., Ind. Eng. Chem., vol. 50, pp. 991 to 992, (1958).

Primary Examiner—Leland A. Sebastian
Attorney, Agent, or Firm—A. C. Ancona

[57] ABSTRACT

A process of making nitroalkanes which comprises reacting a lower alkanol, e.g. methanol, and nitric acid ($HNO_3$) in the vapor phase in the presence of a catalyst which is an oxide or a salt of a metal of Group II of the periodic table, e.g. calcium chloride.

20 Claims, No Drawings

CATALYTIC PREPARATION OF NITROALKANES

BACKGROUND OF THE INVENTION

Nitroalkanes are an essential stabilizing ingredient employed in 1,1,1-trichloroethane when it is used in vapor degreasing and cold cleaning. All manufacturers throughout the world add nitromethane and/or nitroethane to their commercial 1,1,1-trichloroethane-based solvents. Normally nitro-paraffins are manufactured by a vapor phase nitration of the alkane with either nitric acid or $NO_2$. There is a mixture of products formed due to carbon-carbon scission. Thus, for example, when propane is nitrated, the products include 1-nitropropane, 2-nitropropane, nitroethane and nitromethane. Because of the oxidative conditions other oxygen containing compounds are also produced, e.g. aldehydes, acids and carbon oxides. Patents disclosing such a process are U.S. Pat. Nos. 2,844,634 and 2,905,724.

Improvements in these vapor phase nitrations are claimed by employing the nitric acid or nitrogen oxides together with oxygenated sulfur compounds, e.g. $SO_2$, $H_2SO_4$, (U.S. Pat. No. 3,272,874) and by conducting the nitration in the presence of ozone (U.S. Pat. No. 3,113,975).

Other processes involve nitration of paraffins by nitrogen peroxide $(NO_2)_2$ in the presence of oxygen (air) under pressure at 150°–330° C. (U.S. Pat. No. 3,780,115); reacting an olefin with nitric acid in the presence of a lower aliphatic monocarboxylic acid anhydride to produce a nitroester, subsequently reducing it with an alkali borohydride to form the nitroalkane (U.S. Pat. No. 3,706,808) and reacting organic amines with ozone (U.S. Pat. No. 3,377,387).

Another process, the subject of my copending application (with another) Ser. No. 211,017, filed Nov. 28, 1980, now abandoned, is an improvement which reduces the amount of by-products and obtains improved yields of the desired products by the nitrating of paraffins with nitric acid at lower temperatures and pressures in the presence of high intensity light.

In yet another improved vapor phase process methane or ethane is reacted with nitric acid in the presence of an inert diluent gas at high temperatures, >300° C., over a catalyst, e.g. $SrCl_2$ on a low surface area alumina. This is disclosed in my copending application, Ser. No. 352,506, filed Feb. 25, 1982.

The present invention is a departure from known methods in that it employs the reaction of methanol with nitric acid, or $NO_2$ gas, in the vapor phase over a catalyst in a fixed bed.

SUMMARY OF THE INVENTION

A method of making nitroalkanes which comprises passing the vapors of nitric acid and an alkanol together with an inert gas as a diluent over a fixed bed catalyst maintained at a temperature in the range of 150° to 350° C. The catalyst is a halide or an oxide of a Group II metal, e.g. calcium or barium chloride, which may be supported or pelleted.

DETAILED DESCRIPTION OF THE INVENTION

The process for manufacturing lower nitroalkanes, namely those containing 1–3 carbon atoms, according to the present invention involves a vaporization of a lower alkanol and nitric acid, mixing their vapors and passing over a catalyst which is a salt or oxide of a metal from Group II of the periodic table. The methanol and nitric acid are pumped as liquids to individual vaporizers, mixed, and fed to a fixed bed catalyst over which they are transformed into nitromethane. An inert gas e.g. nitrogen, used as a diluent, can be recycled.

The vapors of the alkanol and nitric acid are thoroughly mixed in proportion of 10 to 1 moles of methanol per mole of $HNO_3$, preferably 4 to 2, and this mixture is diluted with an inert gas, e.g. nitrogen, usually about 2 to 15 moles of the inert per mole of methanol. The preferred range is from about 4 to about 10 moles per mole of methanol reactant. Diluent may be selected from inert gases including nitrogen, argon, the carbon oxides, steam and mixtures thereof.

The gas mixture is preferably preheated to a temperature of from about 100° to about 250° C. and the catalyst bed is maintained at a temperature within the range of about 150° to about 350° C., preferably from about 210° to about 260° C.

The catalyst is a supported or pelleted compound of metals of Group II of the periodic table, namely magnesium, calcium, strontium and barium. Salts of these metals, including the chlorides, sulfates, and nitrates may be employed. The oxides of these metals are also useful as catalysts for the reaction. They may be employed separately or in combination. A preferred combination is $CaCl_2/BaCl_2$ in ratios of 1/4 to 4/1 (molar).

Either the oxides or salts may be burdened on an inert support and used in this manner. Methods of making supported catalysts are well known to the art. For example, the support may be impregnated by immersing it in a salt solution or by spraying the solution onto the support. A slurry is used in the case of oxides or insoluble salts.

Pressures employed in the process may be from about 1 to about 150 psig and preferably from about 6 to about 50 psig.

REPRESENTATIVE PREPARATION OF CATALYST

A catalyst was made by immersing an alumina support* in an amount of aqueous $CaCl_2$ solution sufficient to completely wet it. Excess water was evaporated and the catalyst dried. The amount of $CaCl_2$ supplied was sufficient to provide a 21% by wt. loading on the support. Portions were calcined under a nitrogen purge (oxygen excluded) at 150° C., 415° C., 500° C., 600° C., and 700° C. each for a period of 4 hours.

*This was low surface area (<1 $m^2/g$) spherical support of medium porosity manufactured by Norton and designated SA-5205.

EXAMPLE 1

The different portions of the above prepared catalysts were run in the four foot reactor system. Methanol conversion differed only slightly, varying from about 13% to about 22% for the reaction run at 245° C., 5.5 sec contact time with a $MeOH/HNO_3/N_2$ ratio of 4/1/24. Selectivity varied considerably for the reaction under the above conditions as is shown below in tabular form.

| Calcination Temp. (°C.) | % Selectivity to $CH_3NO_2$ |
| --- | --- |
| 150 | 27 |
| 415 | 35 |
| 500 | 40 |
| 600 | 44 |

| Calcination Temp. (°C.) | % Selectivity to $CH_3NO_2$ |
|---|---|
| 700 | 67 |

Thus, the preferred method of preparing the catalyst is to calcine the salt or oxide of the metal on a support for a period of 2 to 10 hours at a temperature of from 500° to 700° C.

USE OF CATALYST

Initial work on this reaction was accomplished using a small one foot by one inch diameter reactor equipped with fluidized sand heat control, pressure and flow controllers, chilled water scrubber column, and an alarm system. A Brooks thermal mass controller was used to meter nitrogen flow. Milton Roy positive displacement pumps were used to meter the methanol and nitric acid flows.

A larger reactor four feet long by ¾ inch diameter was used for later runs. All the other equipment was the same.

EXAMPLE 2

A quantity (370 ml.) of a catalyst prepared according to the above description, calcined at 700° C. for 4 hours and consisting of a 1/1 (atomic ratio of Ca/Ba) mixture of calcium chloride and barium chloride coated at 19.6% by weight on a low surface area alumina support (A-5205) was loaded into the 4-foot stainless steel tube reactor described above and heated to 270° C. with a diluent gas (nitrogen) purging through the system. The pressure was controlled at 7 psig, preheater temperature 185° C., nitrogen flow 4000 cc/min., then nitric acid was started at 0.0076 gram mole/min. rate. Methanol was then started at 0.0301 gram mole/min. rate (4/1/24 $H_3OH/HNO_3/N_2$ mole ratio).

Analysis of the condensed reactor effluent showed a 17% conversion of methanol and a 60% selectivity to nitromethane.

EXAMPLES 3–7

A supported catalyst containing $CaCl_2/CaO$ (1/1 mole ratio) was employed at different reactant ratios, contact times and temperatures to obtain the conversions and selectivities shown in Table I. The support was the same as employed in Examples 1 and 2 above and catalyst loading was 19.7% based on weight of the finished catalyst.

TABLE I

| Ex. No. | Temp. (°C.) | $CH_3OH/HNO_3/N_2$ Ratio | Contact Time (sec.) | Methanol Conversion (%) | Nitromethane Selectivity (%) |
|---|---|---|---|---|---|
| 3 | 263 | 4.74/1/24 | 7.0 | 16.1 | 57.1 |
| 4 | 250 | 4.73/1/24 | 4.6 | 11.9 | 63.5 |
| 5 | 256 | 3.16/1/24 | 3.6 | 18.7 | 53.0 |
| 6 | 255 | 4/1/24 | 3.6 | 21.7 | 45.7 |
| 7 | 284 | 4/1/24 | 6.2 | 17.0 | 71.5 |

EXAMPLES 8–14

In other experiments anhydrous $CaCl_2$ pellets (5 mesh) were used with conditions and results shown in Table II.

TABLE II

| Ex. No. | Pressure (psig) | Bed Temp. (°C.) | MEOH/$HNO_3$/$N_2$ Ratio | Contact Time (sec.) | Methanol Conversion (%) | Selectivity to Nitromethane (%) |
|---|---|---|---|---|---|---|
| 8 | 8.5 | 285 | 1.58/1/24 | 2.61 | 28.5 | 29.5 |
| 9 | " | " | " | 2.15 | 22.0 | 37.6 |
| 10 | " | " | " | 1.83 | 25.2 | 30.4 |
| 11 | " | " | 2.37/1/24 | 2.69 | 17.1 | 48.5 |
| 12 | 7.0 | 342 | 4.39/1/24 | 1.00 | 22.0 | 31.7 |
| 13 | " | 332 | " | 1.16 | 30.1 | 26.6 |
| 14 | " | " | " | " | 30.9 | 24.5 |

EXAMPLES 15–21

In yet other experiments other Group II metals were tested in the small reactor. Conditions under which the reaction was run were preheater temperature 185° C., nitrogen flow 4000 ml/min. and pressure 7 psig. Table III shows the reaction parameters and results:

TABLE III

| Ex. No. | Temp. (°C.) | Catalyst Composition | Contact Time (sec.) | $CH_3OH/HNO_3/N_2$ Mole Ratio | $CH_3OH$ Conv. (%) | $CH_3NO_2$ Select. (%) | Wt.* % Load. |
|---|---|---|---|---|---|---|---|
| 15 | 215 | $BaCl_2$ | 3.7 | 4/1/24 | 12.0 | 64.6 | 18 |
| 16 | 275 | $MgCl_2$ | 4.5 | 3.8/1/24 | 32.7 | 26.5 | 17.7 |
| 17 | 230 | $SrCl_2$ | 4.2 | 3.7/1/24 | 20.8 | 40.9 | 15.5 |
| 18 | " | $CaCl_2/BaCl_2$ | 3.5 | 4/1/24 | 17.0 | 60.0 | 17.6 |
| 19 | 200 | $(BaCl_2)_2/CaCl_2$ | 3.4 | 4/1/24 | 33.0 | 28.0 | 21.3 |
| 20 | 120 | $(CaF_2)_9/CaCl_2$ | 3.4 | 4/1/24 | 23.0 | 19.0 | 20.7 |
| 21 | 230 | $CaBr_2$ | 5.2 | 3.9/1/24 | 14.0 | 23.0 | 19.7 |

*Catalyst loading is based on total weight of salt and support (low surface alumina).

EXAMPLE 22

Finally, a catalyst of 16% $CaCl_2$ on alumina spheres, calcined at 700° C. for 4 hours, employed in the 4-foot reactor at various temperatures, was run at a MeOH/$HNO_3$/$N_2$ ratio of 3.8/1/24, 4 sec. contact time and a pressure of 8 psig. A quantity of 370 ml of catalyst was employed as in Example 1. Results are shown in Table IV.

TABLE IV

| Temp. (°C.) | % Methanol Conversion | % Selectivity to Nitromethane |
|---|---|---|
| 245 | 8.3 | 68.0 |
|  | 9.7 | 60.5 |
| 260 | 11.6 | 53.1 |
|  | 10.0 | 63.1 |
| 272 | 14.6 | 47.7 |

TABLE IV-continued

| Temp. (°C.) | % Methanol Conversion | % Selectivity to Nitromethane |
|---|---|---|
| | 16.3 | 45.3 |

I claim:

1. A process for making nitroalkanes which comprises reacting in the vapor phase a mixture of a lower alkanol and nitric acid, or nitrogen dioxide, and an inert diluent gas in the presence of a catalyst which is an oxide or a salt of at least one metal of Group II of the periodic table.

2. The process of claim 1 wherein the Group II metal is calcium, barium, strontium or magnesium.

3. The process of claim 2 wherein the reactant and diluent gases are preheated.

4. The process of claim 3 wherein the gases are preheated to a temperature of from about 100° to about 250° C. and the reaction temperature is from about 150° to about 350° C.

5. The process of claim 4 wherein the molar ratio of lower alkanol to nitric acid is from about 10/1 to about 1/1.

6. The process of claim 5 wherein the inert diluent gas is present in an amount of from about 2 to about 15 moles based on moles of methanol present.

7. The process of claim 6 wherein the catalyst is an oxide or salt of calcium and barium in combination.

8. The process of claim 7 wherein the lower alkanol contains 1-3 carbons.

9. The process of claim 8 wherein the lower alkanol is methanol or ethanol.

10. The process of claim 9 wherein the inert diluent gas is nitrogen, argon, CO, $CO_2$, steam or mixtures thereof.

11. A process for making nitromethane which comprises reacting in the vapor phase a mixture of methanol, nitric acid and a nitrogen diluent in the presence of a catalyst which is an oxide of at least one of calcium, barium and strontium.

12. The process of claim 11 wherein the temperature of reaction is from about 210° to about 260° C.

13. The process of claim 12 wherein the reactants and diluent nitrogen are preheated.

14. The process of claim 13 wherein the molar ratio of methanol to nitric acid is from about 4/1 to about 1/1.

15. The process of claim 14 wherein the diluent nitrogen is present in an amount of from about 4 to about 10 moles based on moles of methanol present.

16. The process of claim 15 wherein the catalyst has been prepared by calcining at a temperature of from about 500° to about 700° C. for a period of about 2 to about 10 hours.

17. The process of claim 16 wherein the catalyst is a mixture of calcium and barium chlorides.

18. The process of claim 17 wherein the molar ratio of calcium chloride to barium chloride is from about 1/4 to about 4/1.

19. A process for making nitromethane which comprises reacting in the vapor phase a mixture of methanol, nitric acid and an inert gas diluent in the presence of a catalyst which is a mixture of calcium and barium chlorides at a temperature of from about 210° to about 260° C. at a contact time of from about 1 to about 4 seconds and wherein the said catalyst has been prepared by calcining a mixture of an oxide or salt of calcium and barium at a temperature of from about 500° to about 700° C. for a period of from about 2 to about 10 hours.

20. The process of claim 19 wherein the methanol, nitric acid and diluent are preheated.

* * * * *